United States Patent
Ishizawa et al.

(10) Patent No.: US 6,413,475 B2
(45) Date of Patent: Jul. 2, 2002

(54) AUTOMATIC ANALYSIS APPARATUS WITH LIQUID LEVEL DETECTION FUNCTION

(75) Inventors: Masato Ishizawa; Akira Inagaki; Ryuji Tao, all of Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/181,642

(22) Filed: Oct. 29, 1998

(30) Foreign Application Priority Data

Oct. 31, 1997 (JP) .............................................. 9-299913

(51) Int. Cl.[7] .............................. G01N 27/22; B01L 3/02
(52) U.S. Cl. .......................... 422/106; 422/64; 422/67; 422/100; 436/49; 436/54; 436/180; 324/663; 324/664; 73/864.11; 73/864.24
(58) Field of Search .............................. 422/63, 64, 67, 422/82.01, 82.02, 100, 102, 104, 106, 108; 436/49, 54, 180; 324/663, 664; 73/864.24, 864.11, 304 C

(56) References Cited

U.S. PATENT DOCUMENTS

| | | | | |
|---|---|---|---|---|
| 3,635,094 A | * | 1/1972 | Oberli ....................... | 73/423 A |
| 4,326,851 A | * | 4/1982 | Bello et al. ................ | 23/230 R |
| 4,451,433 A | * | 5/1984 | Yamashita et al. ............. | 422/63 |
| 4,736,638 A | * | 4/1988 | Okawa et al. ............ | 73/864.24 |
| 4,749,988 A | * | 6/1988 | Berman et al. ............. | 340/618 |
| 4,897,244 A | * | 1/1990 | Wallace et al. ............. | 422/100 |
| 4,939,925 A | * | 7/1990 | Sakuma et al. .............. | 73/61.4 |
| 4,970,468 A | * | 11/1990 | Ishizawa et al. ............. | 324/662 |
| 5,027,075 A | * | 6/1991 | Harding, Jr. ................. | 324/662 |
| 5,049,826 A | * | 9/1991 | Sasao .......................... | 324/662 |
| 5,254,311 A | * | 10/1993 | Ushikubo ..................... | 422/81 |
| 5,262,731 A | * | 11/1993 | Mizoguchi ................... | 324/663 |
| 5,648,727 A | * | 7/1997 | Tyberg et al. ................ | 324/677 |
| 5,855,851 A | * | 1/1999 | Matsubara et al. ......... | 422/100 |
| 5,866,426 A | * | 2/1999 | Ball ............................. | 436/54 |
| 6,107,810 A | * | 8/2000 | Ishizawa et al. ............ | 324/662 |

* cited by examiner

Primary Examiner—Jeffrey Snay
Assistant Examiner—Kathryn Bex
(74) Attorney, Agent, or Firm—Mattingly, Stanger & Malur, P.C.

(57) ABSTRACT

An automatic analysis apparatus with a liquid level detection function includes a pipetting device for pipetting a liquid sample from a sample cup to a reaction container by using a pipetting probe that serves as a first capacitor electrode. A sample cup holding means serves as a second capacitor electrode having a ground potential. The conductor material is arranged along a direction in which the pipetting probe moves down for pipetting and is separate from the pipetting device. The conductor material has the same ground potential as that of the sample cup holding means and also serves as a second electrode whereby at any one time either of the sample cup holding means and the conductive material serves as a second capacitor electrode in combination with the first capacitor electrode. An a electrical detector is provided for detecting a change of electrode static capacitance between the pipetting probe and the sample cup holding means and between the pipetting probe and the conductive material as of level detection of the liquid sample. Measurement means are also provided for measuring an ingredient of the reaction container.

10 Claims, 4 Drawing Sheets

AUTOMATIC ANALYSIS APPARATUS WITH LIQUID LEVEL DETECTION FUNCTION

BACKGROUND OF THE INVENTION

The present invention relates to an automatic analysis apparatus having a function for pipetting a liquid sample from one container to another container by using a pipetting probe that serves as an electrode for detecting liquid level.

In a conventional automatic analysis apparatus, the liquid sample of a living body such as blood or urine is pipetted from a sample cup to a reaction container on a reaction line, a reagent is pipetted from a reagent bottle to the reaction container corresponding to analysis items of measurement objects, and the mixture of the sample and the reagent is measured by a measuring means such as a photometer.

In the pipetting operation, the tip of the pipetting probe is dipped in the sample liquid of the pipetting object, but the deeper that the tip of the pipetting probe is dipped, the greater than the quantity of the sample liquid adhered to an outer wall of the probe increases, and the contamination becomes significant.

Then, in order to reduce the dipping depth of the pipetting probe as much as possible, a liquid level of the container is detected, and at a position where the tip of the probe reaches a little beneath the liquid level, the probe stops to move down, and the probe is controlled to withdraw a predetermined amount of the sample liquid.

A pipetting probe serves as an electrode for detecting liquid level, and a liquid container holding means serves as the other electrode for detecting liquid level; the liquid level in the container is detected by a change of an electrostatic capacitance between the pipetting probe and the liquid container holding means, as shown in Japanese Patent Laid-open No. 62-289769 (1987) bulletin and Japanese Patent publication No. 6-7112 bulletin (corresponding to U.S. Pat. No. 4,897,244).

In these documents, the pipetting probe is connected to an electric liquid level detecting circuit, and the liquid container holding means is electrically connected to the ground.

Furthermore, relating to the pipetting probe having a metal inner tube and a metal outer tube, Japanese Patent Laid-open No. 7-43369 bulletin is disclosed, in which insulation resistance between the metal inner tube and the metal outer tube is kept in a good condition, whereby the electrostatic capacitance corresponding to the liquid level of the sample is surely detected.

Further relating to a pipetting nozzle serving as one electrode to detect the liquid level of the sample, Japanese Patent Laid-open No. 8-258661 bulletin is disclosed.

SUMMARY OF THE INVENTION

In the automatic analysis apparatus stated above, the sample cup pipetted with the sample liquid corresponding to the pipetting object is mounted on a sample disc as one embodiment of the container holding means.

When all of the sample cups are set to the sample disc, a detecting signal on the basis of the change of the electrostatic capacitance between the pipetting probe and the sample disc is a big value, and the liquid level detection error is very small.

On the other hand, several kinds of the sample cups having different size are used usually. An especially small sample cup may be set on the sample disc directly, and other containers or supporting holding tools are set on the container loading region of the sample disc, or the small sample cup may be mounted indirectly on the top of the other containers or the supporting holding tools.

When a small-sized sample cup having a short overall length is set on the sample disc indirectly, the spatial distance between the sample liquid in the sample cup and the sample disc serving as the electrode for detecting liquid level becomes large, and it becomes impossible to obtain a sufficient detecting signal to recognize the liquid level with which the pipetting probe contacts, such that the liquid level detection is not executed surely.

An object of the present invention is to provide an automatic analysis apparatus which is capable to surely detect a liquid level of the sample liquid of the sample cup, even if the height of the sample cup is different from the height location arranged for the sample cup holding means.

In the automatic analysis apparatus comprising a pipetting device for pipetting a sample liquid from a sample cup to a reaction container by using a pipetting probe that serves as an electrode for detecting a liquid level of the liquid sample, the sample cup holding means serving as another electrode for detecting the liquid level, an electric detecting element for detecting a change of an electrostatic capacitance between said pipetting probe and said sample cup holding means and a measurement means for measuring the contents of the reaction container, the present invention is characterized by comprising a construction such that a conductive material is arranged along a direction to which the pipetting probe is disposed, and said conductive material has an isopotential to the other electrode.

In a desirable embodiment of the present invention, said sample cup holding means are driven so as to transfer said sample cup being held to an aspiration location by said pipetting probe, and said conductive material is arranged apart from said sample cup holding means and in the neighborhood of said sample aspiration location.

This conductive material includes a pair of plate portions which oppose each other, keeping a gap through which said sample cup on said sample cup holding means is able to pass.

Said sample cup holding means and said conductive material are contacted to ground electrically.

In a desirable embodiment of the present invention, a control part is provided for controlling moving down operation of the pipetting probe according to the output of the liquid level detecting signal supplied from an electric circuit based on change of an electrostatic capacitance between the pipetting probe and the conductive material.

The conductive material is arranged in a region between a height location that is lower than a bottom end of the probe when the pipetting probe moves to a horizontal direction and a height location that is higher than the upper end of sample cup holding means.

This conductive material has a part extended in parallel to a direction to which the pipetting probe moves down.

Moreover, the sample cup holding means has an electrical conduction body as another electrode which surrounds the outer wall of the sample cup.

DETAILED DESCRIPTION OF THE PREFERRED EMBODIMENTS

Figure 1:
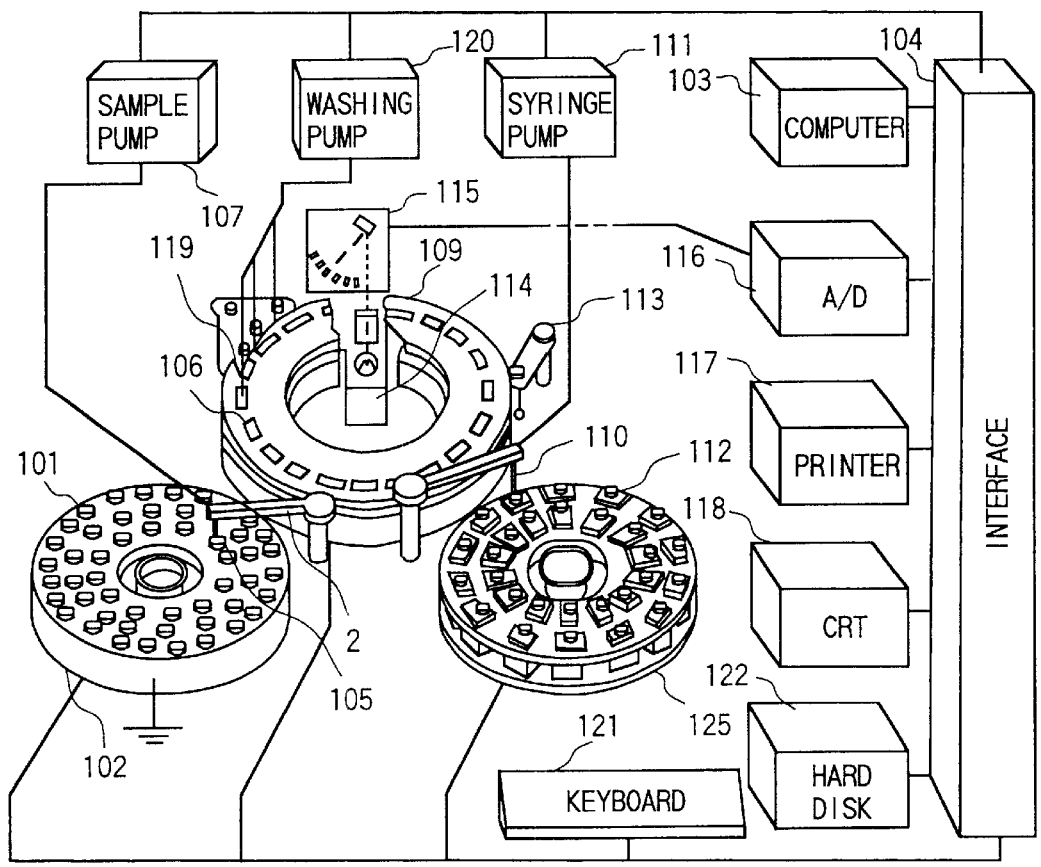
FIG. 1 is a schematic diagram, which shows a total construction of the automatic analysis apparatus of the present invention.

FIG. 1 is a schematic diagram of the total construction of the automatic analysis apparatus in the present invention.

In FIG. 1, the reaction disc 109 is arranged so as to be intermittently rotatable on a water tank kept at a constant temperature.

On the reaction disc 109, a plurality of reaction containers 106 are arranged keeping a circle state, rotation and stopping of the reaction disc 109 are performed at predetermined times, and a line of the reaction container is transferred the retroaction line top.

On a movable arm 2 that is moved vertically and horizontally by a driving department (not shown in the figure), a sample pipetting probe 105 to aspirate and eject the sample is installed.

The sample pipetting probe 105 pipettes the sample from the sample cup 101 to the reaction container 106 on the reaction disc 109 which is mounted on the sample disc 102 top as the sample cup holding means.

Figure 2:
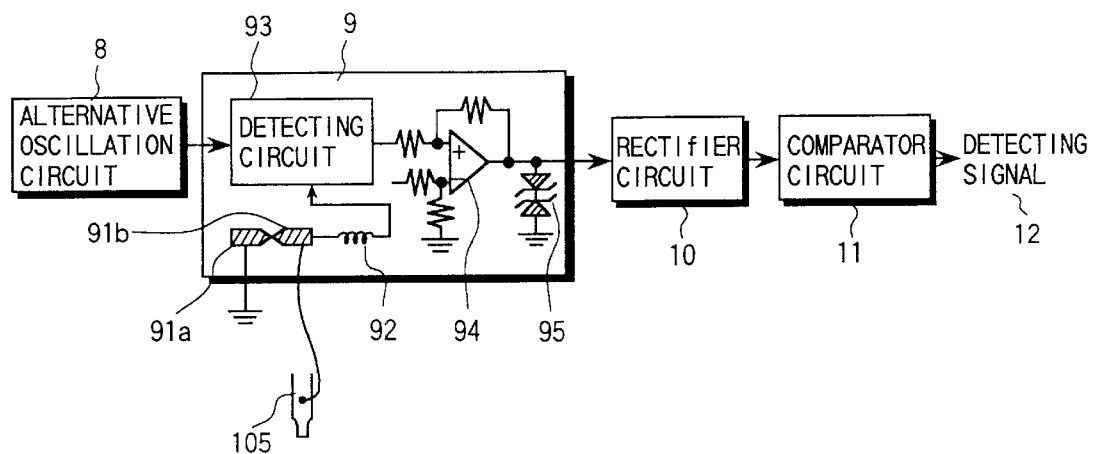
FIG. 2 is an explanatory view of a liquid level detection system in the analysis apparatus of FIG. 1.

Referring to FIG. 2, the construction of a liquid level detection unit will be explained. In FIG. 2, an AC signal output from an AC oscillation circuit 8 is input into a liquid level detecting circuit 9.

As for the AC signal, a sine wave is reasonable, but a square wave or a triangle wave may be replaced.

The liquid level detecting circuit 9 has a detecting circuit 93 to detect a change of an electrostatic capacitance produced between the sample disc 102 connected to ground and the sample pipetting probe 105.

The detecting circuit 93 for detecting the electrostatic capacitance change has a conventional circuit bridge circuit.

The liquid level detecting circuit 9 amplifies the change of the detected electrostatic capacitance, and the AC amplified signal is input into a rectifier circuit 10.

The input AC signal is converted into a direct current signal in the rectifier circuit 10, and is input into a comparator 11.

The comparator 11 compares a change of the input electrostatic capacitance signal with a value before being changed, whereby a detecting signal 12 showing the presence of contact of the pipetting probe 105 with a liquid level in a container, in other words, presence of liquid level detection is provided.

A pair of discharge elements 91a and 91b formed with an electroconductive material on a printed circuit board are disposed to face each other keeping a gap of around 0.1 mm.

Both discharge elements facing each other have peaked tips inside thereof so as to concentrate static electricity thereon and to permit easy discharge of the electricity.

One discharge element 91a of a pair of the discharge elements is contacted to ground electrically.

The other discharge element 91b is electrically connected with the pipetting probe 105 and with the detecting circuit 93 for detecting the electrostatic capacitance change.

In accordance with this construction, the external noise signal caused by electrification of static electricity detected by the pipetting probe 105, is electricity discharged through a pair of discharge elements 91a, 91b to the arm, whereby transmission of the noise signal to the detecting circuit 93 of the electrostatic capacitance change is restrained.

An inductance 92 is mounted between the other discharge element 91b and the electrostatic capacitance change detecting circuit 93 furthermore.

This inductance 92 shows a high impedance characteristic corresponding to high frequency. Therefore, the discharging to the ground of the noise signal is promoted.

The output signal of the detecting circuit 93 for the electrostatic capacitance change goes through an operational amplifier 94.

The amplification factor of the operational amplifier 94 is different corresponding to the smallest detection capacity of the device, however it is several 108-several 100 times generally.

The output AC signal of operational amplifier 94 is converted to a direct current signal by a rectifier circuit 10.

Because, in the example of FIG. 2, the alternating output of the operational amplifier 94 is clamped by Zener diode 95, a sudden signal such as the static electricity noise or other disturbance noise, that is, a useless signal is not transmitted to the rectifier circuit 10, and is not integrated.

Accordingly, a bad affect by the external noise is extremely small.

In the analysis apparatus shown in FIG. 1, the metal pipetting probe 105 which is one electrode for liquid level detection is connected to the liquid level detecting circuit 9, and is electrically contacted with the metal sample disc 102 serving as the other electrode for the liquid level detection.

However, being connected reversibly, that is, in the case that the sample disc is connected to the liquid level detecting circuit, and is contacted with the pipetting probe, a change of the electrostatic capacitance may be detected too.

In the example shown in FIG. 1, the whole body of the sample disc 102 is electrically conductive, however, instead of the above, most of the sample disc 102 may be constituted with a non-electrically conductive matter such as a plastic, and the electrically conductive matter functioning as the electrode for the liquid level detection may be provided in the region which directly contacts a sample cup or closely approaches it, that is, only in the region surrounding the outer wall of the sample cup.

In any event, a holding location of each container in the sample disc 102 is formed as an electrode for detecting the liquid level having a shape to surround the outer wall of the container. Construction of the automatic analysis apparatus shown in FIG. 1 will be explained further.

On a reagent disc 125, which is freely rotatable, a bottle 112 of the reagent is arranged corresponding to plural analysis items as analysis objects.

A reagent pipetting probe 110 installed on the movable arm pipettes the predetermined amount of the reagent from the reagent bottle 112 to a reaction container 106.

The sample pipetting probe 105 executes an aspiration behavior of the sample and a discharge behavior according to the operation of a sample pump 107 for the sample.

Reagent pipetting probe 110 executes an aspiration behavior of the reagent and a discharge behavior with an operation of the syringe pump 111 for the reagent.

The analysis item that should be analyzed for each sample is input from a keyboard 121 or an input unit as a display of CRT 118.

The computer 103 controls an operation of each unit in this automatic analysis apparatus. The sample cup 101 is transferred to a sample aspiration location according to an intermittent rotation of the sample disc 102, the descent of the sample pipetting probe 105 in the sample cup being stopped.

When the tip of the pipetting probe 105 contacts with the liquid level of the sample according to a drop operation thereof, a detecting signal is output from the liquid level detecting circuit 9, whereby the computer 103 controls the drop operation of the drive department of the movable arm 2 to stop.

Subsequently after having aspirated the predetermined amount of the sample in the pipetting probe 105, the pipetting probe 105 rises to top dead center, the mobile arm 2 having the pipetting probe 105 is turned in a horizontal plane, and the sample pipetting probe 105 moves down in a location of the reaction container 106 on the reaction disc 109 and discharges the sample stored in the reaction container 106.

When the reaction container 106 then moves to a position where the reagent should be added, the reagent corresponding to the analysis item is added from the reagent pipetting probe 110. Corresponding to the pipetting of the sample and the reagent, the liquid level of the sample in the sample cup 101 and the reagent in reagent bottle 112 is detected.

The mixture in the reaction container to which the sample and the reagent are added, is stirred by a stirring device 113.

Plural reaction containers cross a light beam from a light source 114 during passage of a line of the reaction container, and an absorbance of each mixture is measured by a photometer 115 as a measurement means.

The absorbance signal goes by way of an analog-to-digital converter 116 and through interface 104, and is transmitted to the computer 103, where the concentration of the analysis item is calculated.

Analysis result prints are output by a printer 117 through the interface 104, or displayed on the CRT 118, and are stored in the hard disk 122 as a memory device.

The reaction container 106 is then washed in a location of the washing mechanism 119.

A pump 120 for washing supplies washing liquid to the reaction container and the disposed waste is drained from the reaction container.

According to the example of FIG. 1, the container holding department is formed on three lines of concentric circles of the sample disc 102 so as to set three lines of the sample cups. A sample aspiration location by the sample pipetting probe 105 is established on each line.

Figure 3:
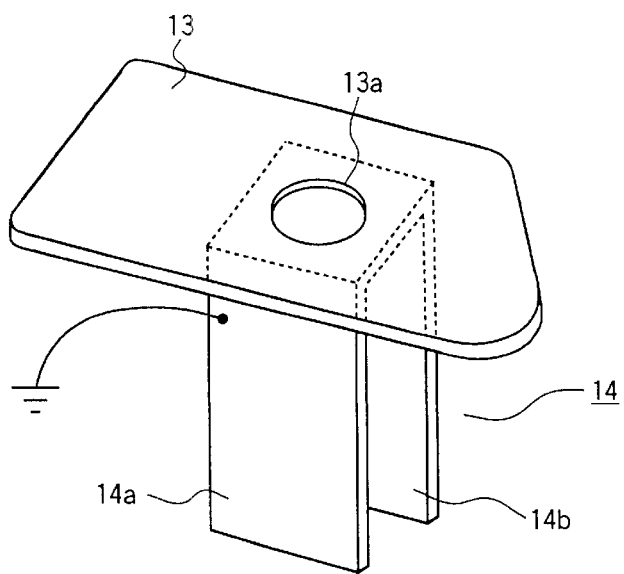
FIG. 3 shows an embodiment of a conductive material used in a pipetting location of the sample.

A conductive material shown in FIG. 3 is arranged so as to correspond to that sample aspiration location.

This conductive material is arranged in a height region which is lower than a probe bottom end of a height location before the sample pipetting probe starts to move down in the sample aspiration location, or a height location just before the sample pipetting probe moves to a horizontal direction.

Further, this conductive material is arranged at the height region higher than the upper end of the sample disc 102 serving as one of the electrodes for the liquid level detection.

The conductive material 14 shown in FIG. 3, is constituted by a metal electrically-conductive plastic or non-electroconductivity electrically-conductive plastic, treated by a metal plating, and is kept to be an isopotential with the sample disc 102.

That is, the conductive material 14 is contacted with ground when the sample disc is electrically contacted with ground.

If the sample disc is a type connected with the liquid level detecting circuit 9 electrically, the conductive material 14 is connected to the liquid level detecting circuit 9 electrically, too.

This conductive material 14 is arranged along a direction to which the sample pipetting probe 105 moves down and up vertically in the sample aspiration location.

The conductive material 14 in FIG. 3 has a pair of plates 14a and 14b arranged to face each other, and is installed and held by a guard or support member 13 that is a part for installation.

Figure 4:
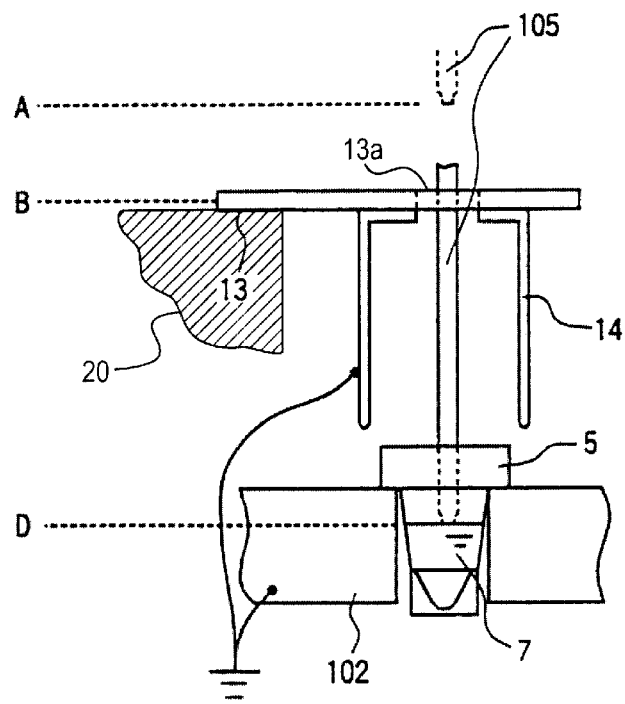
FIG. 4 is an explanatory view of the liquid level detection operation when setting a sample cup directly.
Figure 5:
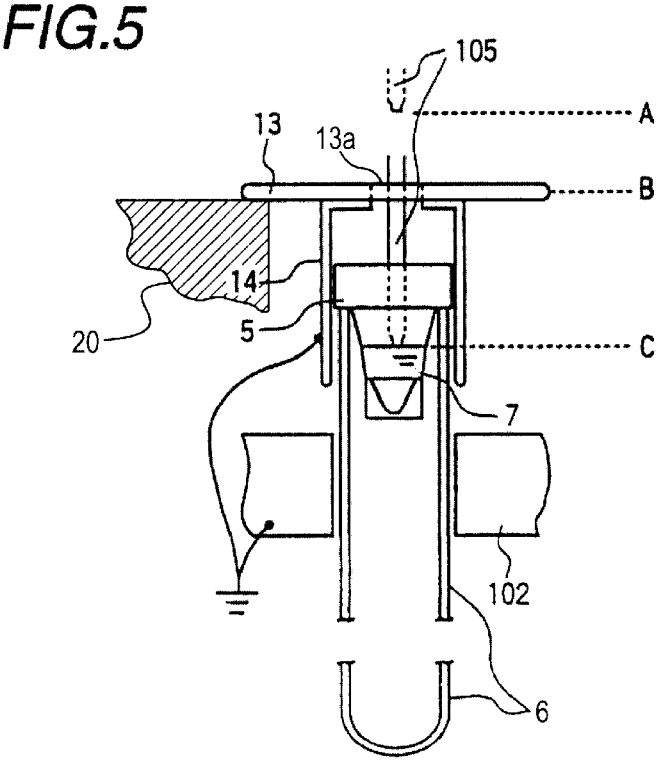
FIG. 5 is an explanatory view of the liquid level detection operation when setting a sample cup indirectly.

A through hole 13a through which the sample pipetting probe 105 may move freely in and out in a vertical direction is formed in the guard 13 and the conductive material 14. The guard 13 is installed to or mounted on a base 20 of the analysis apparatus as shown in FIGS. 4 and 5.

Plates 14a and 14b face each other in parallel, and the gap of them is a distance through which the sample cup 101 on the sample disc 102 may pass, and a distance that may have a function as an electrode for the liquid level detection.

In a circumstance explained in an example of FIG. 3, both plates 14a, 14b are arranged to be parallel, however when being arranged upwards of the sample disc as shown in FIG. 1, they become a shape curved along a transfer locus of the sample cup 101 on each line.

The plates 14a, 14b are extended in a vertical direction so that they are made parallel to the moving up and down direction of the sample pipetting probe 105.

The overall length of the top and bottom direction of plates 14a, 14b, is about half of the overall distance that the sample pipetting probe 105 is capable of moving downward, and is changed depending on the size of the sample cup.

The guard 13 that is a component for installation may be constituted by plastic or the metal.

The guard department 13 is used to prevent a foreign article from approaching the probe during an operation of the sample pipetting probe 105, and especially, to prevent a hand of the operator from contacting the pipetting probe.

FIG. 4 shows a case in which a small-sized sample cup 5 is set in the sample disc 102, and FIG. 5 shows a case in which the sample cup 5 is set in the sample disc 102 intermediately through an auxiliary holding tool.

In the example of FIG. 5, a test tube 6 of 100 mm in overall length is used as the auxiliary holding tool.

When being set as shown in FIG. 5, as the liquid level of the sample 7 in the sample cup 5 leaves from the sample disc 102 physically, it becomes difficult to detect a change of the electrostatic capacitance between the sample disc 102 as an electrode for the liquid level detection and the sample pipetting probe 105.

The conductive material 14 contacted electrically so as to be an isopotential with the sample disc 102 is provided corresponding to the sample aspiration location.

This conductive material 14 is arranged to leave or be spaced from the sample disc 102 and from the sample pipetting probe 105.

The conductive material 14 has a function as an electrode for detecting liquid level, which is similar to the sample disc 102.

Figure 6:
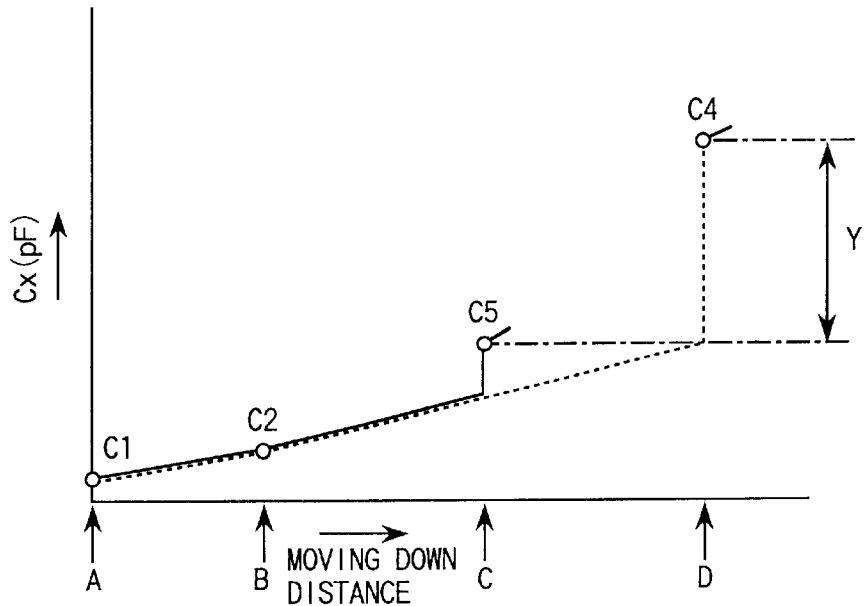
FIG. 6 is an explanaory view of the liquid level detection operation when not applying the present invention.

In a state that a sample cup is set as shown in FIG. 4, when the liquid level of the sample 7 in the sample cup 5 is detected without applying the present invention, that is, when the conductive material 14 is not used, the electrostatic capacitance value between the sample pipetting probe 105 and the sample disc 102 changes as shown by a broken line in FIG. 6.

In FIGS. 4 to 7, the height location A of the sample pipetting probe 105 is the height of the probe bottom end when the pipetting probe is in the greatest rise location (top dead center).

When the sample pipetting probe 105 moves to the reaction container 106 horizontally, it starts to move keeping a state of the height location A.

At the height location B, the bottom end of the pipetting probe 105 in at a height corresponding to the guard 13. The height location C is a height of a liquid level of the sample in a state shown in FIG. 5.

The height location D is in a height of a liquid level of the sample in a state shown in FIG. 4.

Figure 7:
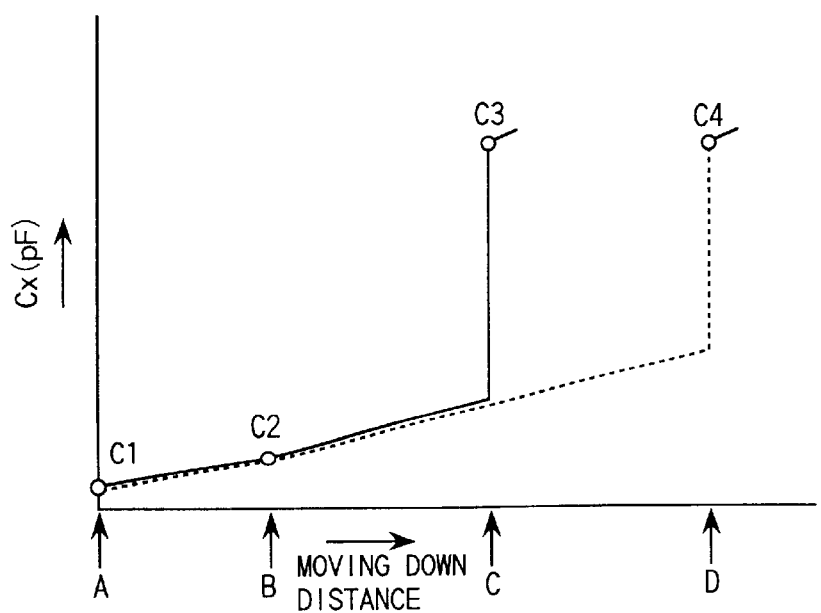
FIG. 7 is an explanaory view of the liquid level detection operation when applying the present invention.

Moreover, in FIGS. 6 and 7, the horizontal scale shows a dropping distance of the pipetting probe, and the vertical scale shows the electrostatic capacitance value Cx (pico farad).

According to the dropping distance from the greatest rise location of the sample pipetting probe 105, a floating capacitance of the guard 13 and the sample disc 102 are added to the pipetting probe, and the electrostatic capacitance value added to the pipetting probe 105 changes as C1, C2, C4 on a broken line shown in FIG. 6.

The electrostatic capacitance value suddenly changes when it drops to the liquid level height location D.

On the contrary, when the sample cup 5 is set as shown in FIG. 5, and the conductive material 14 in the present invention is not used, the electrostatic capacitance value changes as C1, C2, C5 on a solid line shown in FIG. 6.

In other words, even if the bottom end of the sample pipetting probe 105 contacts with the liquid level of the sample 7 (it comes into contact with the height location C), the change of the electrostatic capacitance value is small.

This is because the sample cup 5 is physically separated from the sample disc 102 that is one of the electrodes used for detecting the liquid level, and it becomes difficult to detect the change, because the change of the electrostatic capacitance is small.

Furthermore, it is difficult to set up a threshold for the liquid level detection because a difference y of the electrostatic capacitance value of c4 and c5 is large.

Referring to FIGS. 4, 5 and 7, the liquid level detection operation of the present invention will be explained in the next.

At first, in a state setting the sample cup 5 as shown in FIG. 4, the conductive material 14 does not participate in the liquid level detection, and the sample disc 102 participates in the liquid level detection as one electrode.

When the sample pipetting probe 105 moves down from the greatest height location A, the electrostatic capacitance value changes as shown by a broken line in FIG. 7, and when the tip of the probe contacts with the liquid level of the sample at the height location D, it becomes the electrostatic capacitance value C4.

Such a change is almost equal to the case shown by the broken line of FIG. 6.

According to the output of the liquid level detecting signal 12, the computer 103 that is a control part controls the drive department so as to stop the moving down of the movable arm 2.

In a setting state of the sample cup 5 as shown in FIG. 5 next, the sample disc 102 does not participate in the liquid level detection substantially, and the change of the electrostatic capacitance between the conductive material 14 that is one electrode for detecting the liquid level and the sample pipetting probe 105 is detected by the liquid level detecting circuit 9.

When the sample pipetting probe 105 gradually moves down from the greatest height location A, the electrostatic capacitance value changes as C1, C2, C3 on a solid line shown in FIG. 7.

When the tip of the sample pipetting probe 105 contacts with the liquid level of the sample 7 in the sample cup 5 mounted on the test tube 6, the electrostatic capacitance value suddenly changes to become C3 at the height location C.

This electrostatic capacitance value C3 is almost the same as the value C4 provided with the setting state shown in FIG. 4, and the threshold setting for the liquid level detection is easy.

The liquid level detecting signal 12 is output with the change of the electrostatic capacitance, and the computer 103 controls it so that the moving down operation of the movable arm 2 stops.

Subsequently, a predetermined amount of the sample is aspirated in the sample pipetting probe 105.

When the sample cup 5 is indirectly set to the sample disc by using an auxiliary holding tool such as the test tube 6, the setting height of the sample cup 5 changes according to the size of the auxiliary holding tool.

Moreover, the liquid level height of the sample 7 changes by repeating the pipette operation, too.

The conductive material 14 is arranged so as to be extended along the moving down direction of the pipetting probe, and it is constituted to almost exist along the overall length of the sample cup 5. Further, even if the liquid level height changes, the liquid level may be detected surely.

According to the present invention, even if holding heights of sampling containers are different from each other, it becomes possible to detect the electrostatic capacitance change surely in the case when the pipetting probe contacts with the sample liquid level, whereby the liquid level detection may be performed with high accuracy.

What is claimed is:

1. An automatic analysis apparatus with a liquid level detection function, comprising:

a pipetting device for pipetting a liquid sample from a sample cup to a reaction container by using a pipetting probe that serves as a first capacitor electrode;

a sample cup holding means serving as a second capacitor electrode having a ground potential;

a conductive material arranged over said sample cup holding means and along a direction in which said pipetting probe moves down for pipetting and being separate from said pipetting device, said conductive material being arranged to exist along an overall length of said sample cup when said sample cup is indirectly set to said sample cup holding means by using an auxiliary holding means, said conductive material having the same ground potential as that of said sample cup holding means and also serving as said second capacitor electrode, whereby both said sample cup holding means and said conductive material serve as the second capacitor electrode in combination with said first capacitor electrode;

an electrical detector for detecting a change of electrostatic capacitance between said pipetting probe and said sample cup holding means and said conductive material as a level of detection of said liquid sample; and measurement means for measuring an ingredient of said reaction container.

2. An automatic analysis apparatus with a liquid level detection function as defined in claim 1, wherein:

said sample cup holding means is driven to transfer said sample cup to a sample aspiration location aspirated by said pipetting probe, and said conductive material is arranged to be separated from said sample cup holding means and to be located at said sample aspiration location.

3. An automatic analysis apparatus with a liquid level detection function as defined in claim 1, wherein:

said conductive material comprises a pair of opposed plates having a gap therebetween through which said sample cup on said sample cup holding means passes.

4. An automatic analysis apparatus with a liquid level detection function as defined in claim 1, wherein:

said sample cup holding means and said conductive material are respectively electrically contacted with ground.

5. An automatic analysis apparatus with a liquid level detection function as defined in claim 1, wherein:

said conductive material has a hole through which said pipetting probe moves up and down, and has a guard member to prevent any article from being close to said pipetting probe.

6. An automatic analysis apparatus with a liquid level detection function as defined in claim 1, wherein:

said conductive material is arranged in a region between a height location that is lower than a height location of a bottom end of said pipetting probe when said pipetting probe moves in a horizontal direction, and a height location that is higher than an upper end of said sample cup holding means.

7. An automatic analysis apparatus with a liquid level detection function as defined in claim 1, further comprising:

a controller for controlling the moving down operation of said pipetting probe according to a liquid level detecting signal output from said electrical detector based on said change of electrostatic capacitance between said pipetting probe and said sample cup holding means and said conductive material.

8. An automatic analysis apparatus with a liquid level detection function as defined in claim 1, wherein:

said conductive material has a part extended in parallel to said direction in which said pipetting probe moves down.

9. An automatic analysis apparatus with a liquid level detection function as defined in claim 1 wherein said conductive material is mounted on a base of said automatic analysis apparatus separate from said pipetting device.

10. An automatic analysis apparatus with a liquid level detection function as defined in claim 9 wherein said conductive material is mounted on said base by a support member.

* * * * *